United States Patent
Yadav

(10) Patent No.: US 9,403,746 B2
(45) Date of Patent: *Aug. 2, 2016

(54) CROSS-LINKED POLYMER ELECTROLYTE MEMBRANES AND CROSSLINKING MONOMER

(71) Applicant: Nissan North America, Inc., Franklin, TN (US)

(72) Inventor: Rameshwar Yadav, Farmington, MI (US)

(73) Assignee: NISSAN NORTH AMERICA, INC., Franklin, TN (US)

( * ) Notice: Subject to any disclaimer, the term of this patent is extended or adjusted under 35 U.S.C. 154(b) by 128 days.

This patent is subject to a terminal disclaimer.

(21) Appl. No.: 14/446,429

(22) Filed: Jul. 30, 2014

(65) Prior Publication Data

US 2016/0031782 A1 Feb. 4, 2016

(51) Int. Cl.
*C07C 43/166* (2006.01)
*H01M 8/10* (2016.01)
*C07C 43/176* (2006.01)

(52) U.S. Cl.
CPC ............ *C07C 43/166* (2013.01); *C07C 43/176* (2013.01); *H01M 8/1023* (2013.01); *H01M 8/1039* (2013.01); *H01M 8/1058* (2013.01); *H01M 2008/1095* (2013.01); *H01M 2300/0082* (2013.01); *H01M 2300/0088* (2013.01)

(58) Field of Classification Search
CPC ............ H01M 2008/1095; H01M 2300/0082; H01M 8/1025; H01M 8/1027; H01M 8/1072; H01M 8/1018; H01M 8/102
See application file for complete search history.

(56) References Cited

U.S. PATENT DOCUMENTS

| | | | |
|---|---|---|---|
| 6,117,961 A | 9/2000 | Ogawa | |
| 7,435,495 B2 | 10/2008 | DeSimone et al. | |
| 7,449,112 B2 | 11/2008 | Lee et al. | |
| 8,652,706 B2 | 2/2014 | Song | |
| 2001/0007890 A1 | 7/2001 | Niessner et al. | |
| 2006/0281824 A1 | 12/2006 | Asano et al. | |
| 2011/0046247 A1 | 2/2011 | Roelofs et al. | |

OTHER PUBLICATIONS

Patrick H. Toy, Thomas S. Reger, Patrick Garibay, Jayne C. Garno, J. A. Malikayil, Gang-yu Liu, and Kim D. Janda. Polytetrahydrofuran Cross-Linked Polystyrene Resins for Solid-Phase Organic Synthesis, J. Comb. Chem. 2001, 3, 117-124.*

Jia Deng, Cuifen Lu, Guichun Yang, Zuxing Chen. Preparation of microgel-supported chiral catalysts and their application in the asymmetric hydrogenation of aromatic ketones, Reactive & Functional Polymers 72 (2012) 378-382.*

Zhou, Zhilian, et al.; "Molded, High Surface Area Polymer Electrolyte Membranes from Cured Liquid Precursors", JACS Articles, J. Am. Chem. Soc. 2006, 128, pp. 12963-12972, Sep. 12, 2006.

Yildiz, Ufuk, et al.; "Free Radical Crosslinking Copolymerization. Gelation Behavior of Macromonomeric Azoinitiators Versus Macrocrosslinkers", Macromol. Chem. Phys. 199, pp. 163-168 (1998).

Yadav, Rameshwar, et al.; "Chemically Crosslinked Polymer Electrolyte Membranes from Fluorinated Liquid Precursors for Application in Fuel Cells", Dissertation submitted to the Graduate Faculty of North Carolina State University, Chemical Engineering, Raleigh, North Carolina, 2010, Chapters 4 and 5.

Kharas, Gregory et al., Novel Copolymers of 4-Fluorostyrene.7. Halogen Ring-Disubstituted 2-phenyl-1, 1-dicyanoethylenes, 2011, Journal of Macromolecular Science, Part A: Pure and Applied Chemistry, 48, 95-99.

* cited by examiner

*Primary Examiner* — Carlos Barcena
(74) *Attorney, Agent, or Firm* — Young Basile Hanlon & MacFarlane, P.C.

(57) ABSTRACT

Bifunctional styrenated crosslinkable monomers are produced by functionalizing a linear chain diol with styrene, the linear chain diol being a diol with linear chain fluorinated segments or a linear chain hydrocarbon diol. Crosslinked polymers are produced by polymerizing the styrene-based comonomer with the bifunctional styrenated crosslinkable monomers. Polymer electrolyte membranes are produced from the crosslinked polymers. Crosslinking a bifunctional fluorinated monomer with a sulfonic acid bearing comonomer produces crosslinked polymers and membranes there from with very high acid content and strong polymer structure.

18 Claims, 1 Drawing Sheet

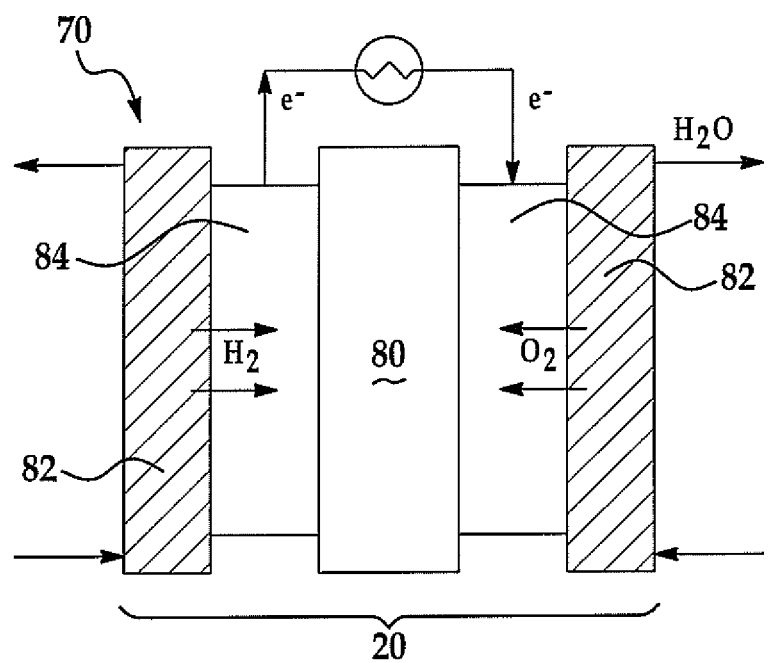

CROSS-LINKED POLYMER ELECTROLYTE MEMBRANES AND CROSSLINKING MONOMER

TECHNICAL FIELD

This disclosure relates to novel cross-linked styrene-based electrolyte membranes, and in particular to cross-linked polymer electrolyte membranes produced by crosslinking bifunctional fluorinated monomers with a sulfonic acid bearing co-monomer.

BACKGROUND

PEM fuel cells (PEMFCs) generate power from electrochemical conversion of fuels such as hydrogen and hydrocarbons at its anode and oxidants such as oxygen and air at its cathode using a membrane as electrolyte. The membrane acts both as a proton conductor and a barrier between the fuel and oxidants. Developing a membrane with high ionic conductivity at high temperature and low relative humidity (RH %) is desired to simplify the humidification system and operation, improve fuel cell performance, and reduce the cost for early commercialization of fuel cell electric vehicles. Current state-of-the-art membranes such as Nafionri membranes and other perfluorosulfonic acid (PFSA) membranes have reasonable conductivity at high RH % and at temperatures below 100° C. However, these membranes hold less water at low RH % and undergo permanent thermal degradation at temperatures above 100° C.

In these membranes, conductivity at low RH % could be improved by increasing the acid content (—$SO_3H$ group) or by reducing the equivalent weight (EW). However, increasing the acid content beyond certain values leads to polymer dissolution, weak mechanical structure, and eventually failure of the membrane in fuel cells. The linear-chain-structure in current state-of-the-art PFSA membranes is inadequate to allow acid content beyond certain values. Without increasing the acid content and preventing polymer structure damage at high temperature, current state-of-the-art PFSA membranes are unable to function at low RH % and at high temperature. In addition, these current PFSA membranes are manufactured under extremely high reaction conditions using sophisticated equipment and processes that make them difficult and expensive to produce.

SUMMARY

Disclosed herein are bifunctional styrenated crosslinkable monomers produced by functionalizing a linear chain diol with styrene, the linear chain diol being a diol with linear chain fluorinated segments or a linear chain hydrocarbon diol.

Also disclosed herein are crosslinked polymers produced by polymerizing a styrene-based comonomer with the bifunctional styrenated crosslinkable monomers produced by functionalizing a linear chain diol with styrene.

Also disclosed herein are polymer electrolyte membranes comprised of the crosslinked polymers. Crosslinking a bifunctional fluorinated monomer with a sulfonic acid bearing comonomer produces crosslinked polymers and membranes there from with very high acid content and strong polymer structure.

These and other aspects of the present disclosure are disclosed in the following detailed description of the embodiments, the appended claims and the accompanying figures.

BRIEF DESCRIPTION OF THE DRAWINGS

The various features, advantages and other uses of the present apparatus will become more apparent by referring to the following detailed description and drawing in which:

FIG. 1 is a schematic of a membrane electrode assembly of a fuel cell incorporating a crosslinked polymer as disclosed herein.

DETAILED DESCRIPTION

The inventors' objective of developing PFSA membranes capable of functioning at low RH % and at high temperature is realized by their development of styrenated crosslinkable monomers and the crosslinked polymers produced from the inventive monomers. The bifunctional styrene-based liquid monomers disclosed herein have a very strong middle segment that can be readily produced without the need for extremely high reaction conditions and the sophisticated equipment and processes that renders production difficult and expensive. The styrenated crosslinkable monomers can easily be polymerized with many types of comonomer to develop varieties of membranes. The crosslinked polymers disclosed herein provide membranes with very low equivalent weight that can retain the morphological structure at high temperatures while maintaining conductivity at low RH %.

The inventors have discovered that when crosslinkers, such as some commercially available crosslinkers, with fragile or weak middle segments are used to develop membranes, these membranes are not mechanically strong. In addition, these crosslinkers do not allow for the increase in acid content in the membrane. In some instances, acid bearing side groups of membranes are also ionically crosslinked. But this type of crosslinking is not stable and unravels under liquid water and high temperature.

The styrenated crosslinkable monomers disclosed herein have a strong middle segment to prevent dissolution of the membrane, resulting in a crosslinked polymer having a fluorinated segment between benzene and —$SO_3H$ that is highly acidic. No weak middle segments are incorporated between the two end reactive groups to fabricate the membrane. The membranes disclosed herein, produced with the styrenated crosslinkable monomers and a compatible comonomer, incorporate acid functionality to the membrane. The disclosed styrenated crosslinkable monomers can be used to develop other types of polymer materials as well.

The styrenated crosslinkable monomers disclosed herein have the following formula, where X is F or H.

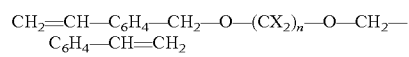

One of the styrenated crosslinkable monomers disclosed herein is styrenated perfluoro alkane (SPA) having the following formula:

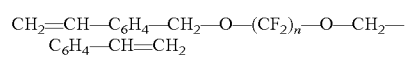

SPA is produced using a diol with a linear chain fluorinated segment having the following formula, where n=6-14:

One example of such a diol is 1H,1H,12H,12H-perfluoro-1,12-dodecanediol. The SPA is produced by functionalizing the diol with the linear chain fluorinated segment with styrene. Functionalizing can be done by mixing the diol with vinyl benzyl chloride, for example. The diol and vinyl benzyl chloride can be mixed in a solvent and reacted using a base such as potassium hydroxide to functionalize the diol with styrene at both ends, with the reaction carried out at room temperature until completion. The product is quenched with an acid and filtered. The filtered product is dried and the SPA is precipitated using diethyl ether. The SPA is highly reactive, warranting storage at very low temperature.

Another of the styrenated crosslinkable monomers disclosed herein is styrenated hydrocarbon alkane (SHA) having the following formula:

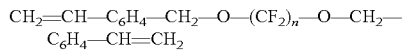
$CH_2=CH-C_6H_4-CH_2-O-(CF_2)_n-O-CH_2-C_6H_4-CH=CH_2$

SHA is produced using a linear chain hydrocarbon diol having the following formula, where n=6-18: $OH-CH_2-(CH_2)_n-CH_2-OH$.

One example of such a diol is 1,12-dodecanediol. The SHA is produced by functionalizing the hydrocarbon diol with styrene. Functionalizing can be done by mixing the hydrocarbon diol with vinyl benzyl chloride, for example. The diol and vinyl benzyl chloride can be mixed in a solvent and reacted using a base to functionalize the diol with styrene at both ends, with the reaction carried out at room temperature until completion. The product is quenched with an acid and filtered. The filtered product is dried and the SHA is precipitated using diethyl ether. The SHA is highly reactive, warranting storage at very low temperature.

Crosslinked polymers can be produced from the styrenated crosslinkable monomers SPA and SHA, thereby producing membranes with very low equivalent weight that can retain the morphological structure at high temperatures while maintaining conductivity at low RH %. Such crosslinked polymers are produced by polymerizing a styrene-based comonomer with either SPA or SHA. The crosslinked polymer will have the following Structure 1, with X=F or H depending on whether SPA or SHA is used.

Structure 1

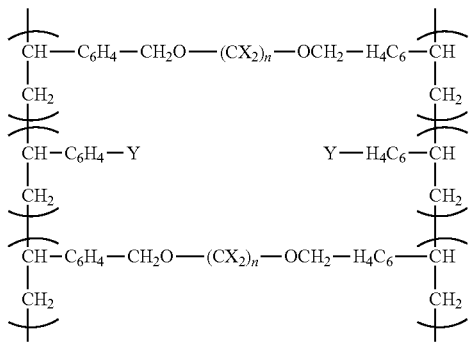

In the crosslinked polymer formula above, Y is $SO_3H^+$ or $R_f-SO_3H^+$ or $-O-R_f-SO_3H^+$, depending on the styrene-based comonomer used and the polymerization process used. If $Y=R_f-SO_3H^+$ or $-O-R_f-SO_3H^+$, then $R_f=-(CF_2)_m-O-CF_2CF_2-$ and m=2-7. Specific examples of crosslinked polymers will be described herein under Examples.

To develop a pure fluorinated membrane, the crosslinked polymer of Structure 1 can be fluorinated with elemental fluorine gas to convert hydrogen elements into fluorine, resulting in a fluorinated crosslinked polymer having the following Structure 2:

Structure 2

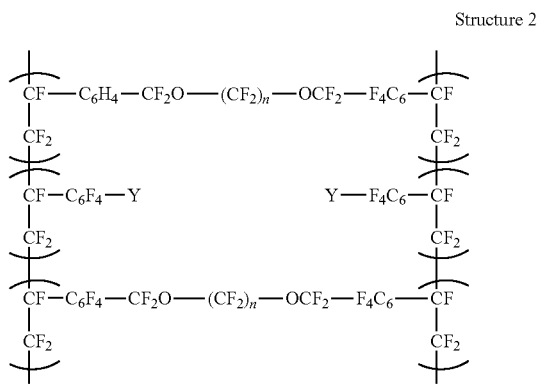

The crosslinked polymers in Structure 1 and the fluorinated crosslinked polymers in Structure 2 can incorporate free-radical scavengers to improve the chemical durability of the membranes during, for example, open circuit voltage hold conditions. Free-radical scavengers such as 4-hydroxy styrene or 4-vinylaniline are co-added with the styrene-based comonomer to neutralize the free-radicals (OH, OOH) responsible for chemical degradation of membrane. Although cerium oxide or other inorganic additives have been added in polymer electrolyte membranes to improve chemical durability, these additives can leach out from the membrane, compromising the durability. It is believed that the polymer based additives (4-hydroxy styrene or 4-vinyl aniline) used as free-radicals scavengers to improve the durability are more stable than the inorganic fillers in the membrane. The crosslinked polymer in Structure 1 polymerized with one of 4-hydroxy styrene or 4-vinylaniline as a free-radical scavenger will result in the crosslinked polymer shown in Structure 3, where $Z=OH$ or $NH_2$:

Structure: 3

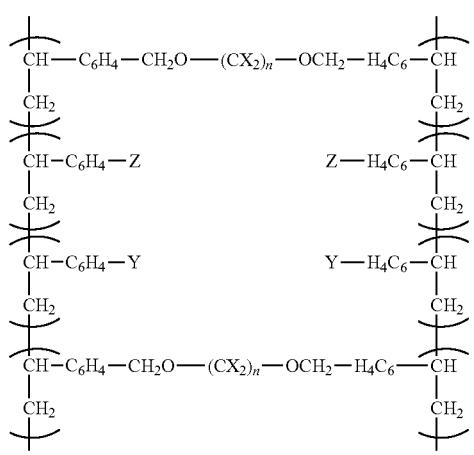

The crosslinked polymers shown in any of Structure 1, 2 or 3 can be used to produce a polymer electrolyte membrane for use in a fuel cell, for example. To fabricate a composite membrane, the crosslinked polymer is imbibed into a porous support, including ePTFE, a nanofiber support or any other support, polymerized, hydrolyzed, and ion-exchanged.

The SPA and SHA styrenated crosslinkable monomers can also be used to produce crosslinked membranes for alkaline fuel cells and direct methanol fuel cells. For alkaline fuel cells, a comonomer such as vinyl benzyl trimethyl chloride/hydroxide can be polymerized with SPA or SHA to produce an ion exchange membrane with very low equivalent weight, high conductivity, and a strong structure. These styrenated crosslinkable monomers can also be used with other types of comonomers to develop an ion exchange membrane. For direct methanol fuel cells, crosslinked membranes can be developed with low equivalent weight and strong structure because direct methanol fuel cells also use proton exchange membranes similar to hydrogen fuel cells. Since SPA and SHA are styrene-based bifunctional monomers and styrene has very high reactivity and is easily polymerizable, they can also be copolymerized with many types of compatible non-styrene based comonomers to develop crosslinked polymers.

FIG. 1 illustrates the use of a membrane produced with a crosslinked polymer disclosed herein. FIG. 1 is a schematic of a fuel cell 70, a plurality of which makes a fuel cell stack. The fuel cell 70 is comprised of a single membrane electrode assembly 20. The membrane electrode assembly 20 has a membrane 80 made from a crosslinked polymer disclosed herein, the membrane 80 coated with catalyst 84 with a gas diffusion layer 82 on opposing sides of the membrane 80. The membrane 80 has a catalyst layer 84 formed on opposing surfaces of the membrane 80, such that when assembled, the catalyst layers are each between the membrane 80 and a gas diffusion layer 82. Alternatively, a gas diffusion electrode is made by forming one catalyst layer 84 on a surface of two gas diffusion layers 82 and sandwiching the membrane 80 between the gas diffusion layers 82 such that the catalyst layers 84 contact the membrane 80. When fuel, such as hydrogen gas (shown as $H_2$), is introduced into the fuel cell 70, the catalyst layer 84 of the catalyst coated membrane 80 splits hydrogen gas molecules into protons and electrons. The protons pass through the membrane 80 to react with the oxidant (shown as $O_2$), such as oxygen or air, forming water ($H_2O$). The electrons (e), which cannot pass through the membrane 80, must travel around it, thus creating the source of electrical energy.

Examples of crosslinked polymers produced by one of the styrenated crosslinkable monomers disclosed herein and for use in polymer electrolyte membranes are described in greater detail. Each of the crosslinked polymers described below can be fluorinated as shown in Structure 2, and/or can be produced with free-radical scavengers, as shown in Structure 3.

A crosslinked polymer is produced by mixing the desired ratio of SPA with styrene sulfonic acid comonomer having the formula $CH_2=CH-C_6H_4-SO_3H^+$, along with a free-radical initiator such as azobisisobutyronitrile (AIBN) or benzoyl peroxide to initiate the polymerization reaction, the mixture polymerized under heat or UV light. The resulting crosslinked polymer has the following Structure 4:

Structure 4
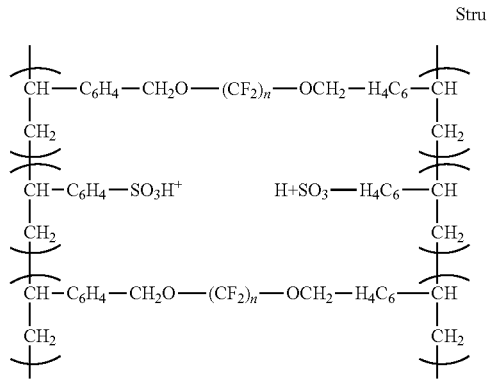

The crosslinked polymer shown in Structure 4 is also produced by mixing the desired ratio of SPA with styrene sulfonate-sodium comonomer having the formula $CH_2=CH-$ $C_6H_4-SO_3Na^+$, the mixture polymerized under heat or UV light. The intermediate polymer structure shown below

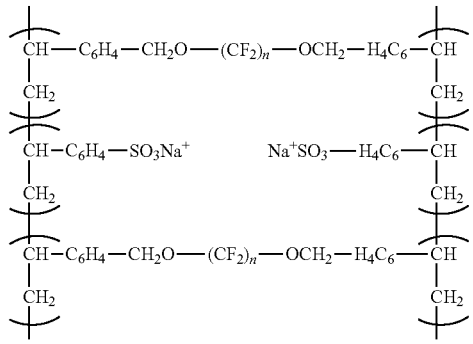

further undergoes ion exchange with an acid solution to produce the crosslinked polymer shown in Structure 4.

Another crosslinked polymer is produced by mixing the desired ratio of SPA with styrene sulfonyl halide comonomer having the formula $CH_2=CH-C_6H_4-SO_2Cl$ or $CH_2=CH-C_6H_4-SO_2F$, the mixture polymerized under heat or UV light. The intermediate polymer structure shown below:

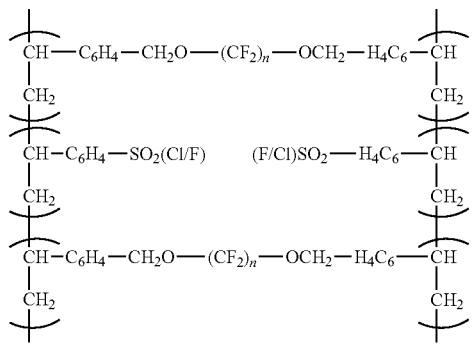

is hydrolyzed with a base/alcohol solution and undergoes ion exchange with an acid solution to produce the crosslinked polymer shown in Structure 4.

To produce the crosslinked polymer shown in Structure 4 with free-radical scavengers, $CH_2=CH-C_6H_4-OH$ or $CH_2=CH-C_6H_4-NH_2$ is added at 1-2 wt % to the mixture during polymerization, resulting in a crosslinked polymer having free-radical scavengers, shown in Structure 5 below:

Structure 5
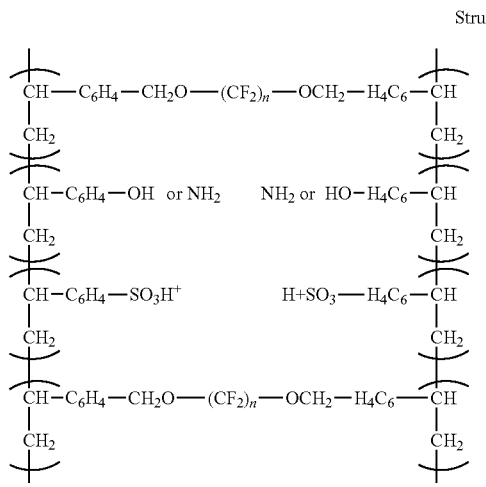

Another crosslinked polymer is produced by mixing the desired ratio of SPA with 4-Bromo styrene comonomer having the formula $CH_2=CH—C_6H_4—Br$, the mixture polymerized under heat or UV light. The intermediate polymer structure shown below

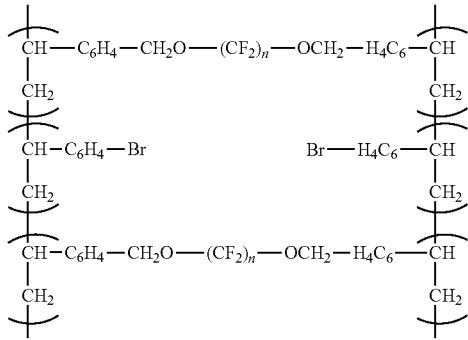

is reacted with $I—(CF_2)_m—O—CF_2—CF_2—SO_2F$, where m=2-7, under heat and in the presence of copper or copper oxide catalyst to produce a second intermediate polymer structure shown below in Structure 6:

Structure 6

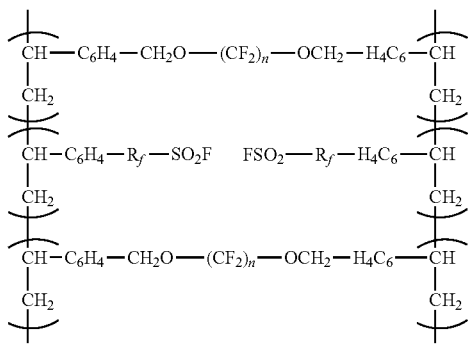

The second intermediate polymer structure is hydrolyzed with a base/alcohol solution and undergoes ion exchange with an acid solution to produce the crosslinked polymer shown in Structure 7 below, where $R_f=-(CF_2)_m—O—CF_2CF_2—$ and m=2-7.

Structure 7

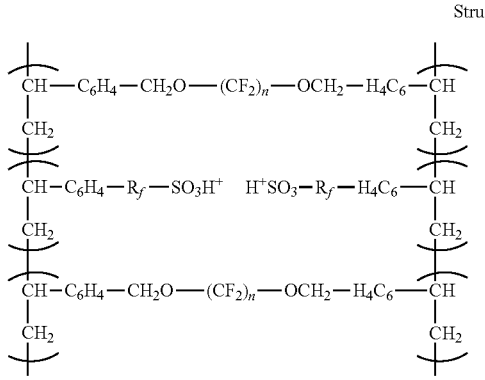

Another crosslinked polymer is produced by mixing the desired ratio of SPA with 4-hydroxy styrene comonomer having the formula $CH_2=CH—C_6H_4—OH$, the mixture polymerized under heat or UV light. The intermediate polymer structure shown below

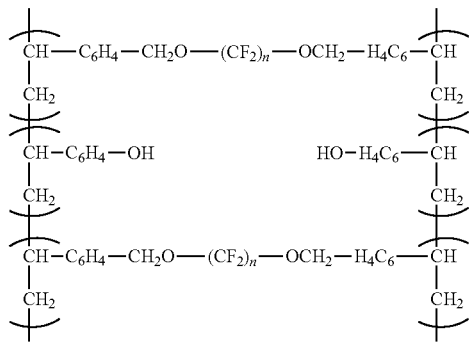

is reacted with $I—(CF_2)_m—O—CF_2—CF_2—SO_2F$, where m=2-7, under heat and in the presence of copper or copper oxide catalyst to produce a second intermediate polymer structure shown in Structure 8.

Structure 8

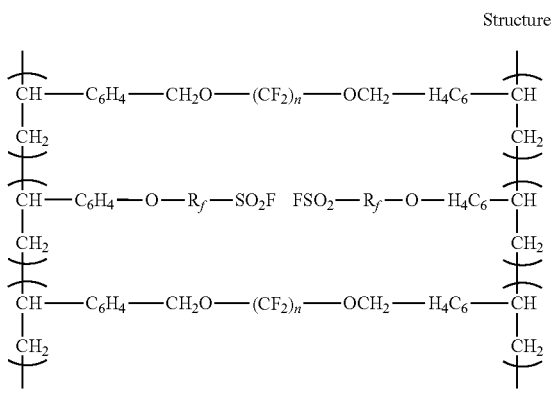

The second intermediate polymer structure is hydrolyzed with a base/alcohol solution and undergoes ion exchange with an acid solution to produce the crosslinked polymer shown in Structure 7, where, again, $R_f=-(CF_2)_m—O—CF_2CF_2—$ and m=2-7.

To produce the crosslinked polymer shown in Structures 7 or 8 with free-radical scavengers, 4-vinyl aniline ($CH_2=CH—C_6H_4—NH_2$) is added at 1-2 wt % to the mixture during polymerization, resulting in a crosslinked membrane structure having free-radical scavengers. Structure 9, below, illustrates the crosslinked polymer of Structure 7 with free-radical scavengers:

Structure 9

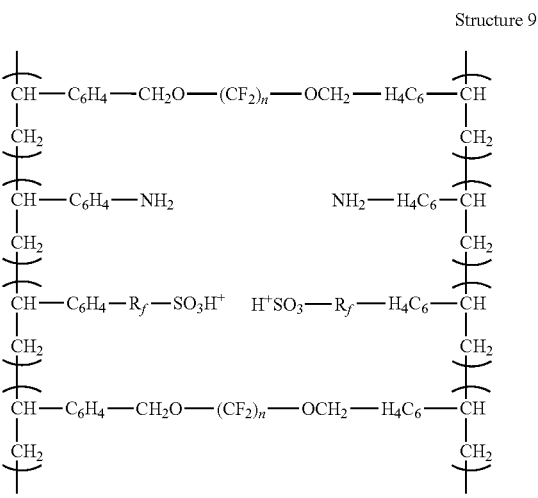

Similar crosslinked polymers are produced using SHA rather than SPA. A crosslinked polymer is produced by mixing the desired ratio of SHA with styrene sulfonic acid comonomer having the formula $CH_2=CH-C_6H_4-SO_3H^+$, the mixture polymerized under heat or UV light. The resulting crosslinked polymer has the following Structure 10:

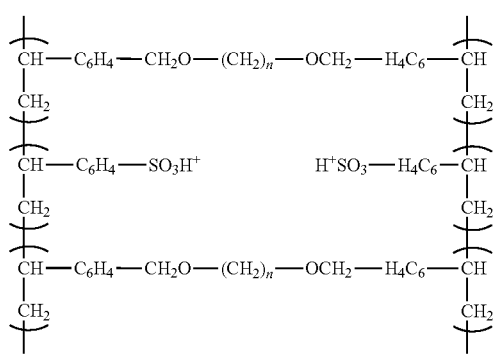

Structure 10

The crosslinked polymer shown in Structure 10 is also produced by mixing the desired ratio of SHA with styrene sulfonate-sodium comonomer having the formula $CH_2=CH-C_6H_4-SO_3Na^+$, the mixture polymerized under heat or UV light. The intermediate polymer structure shown below

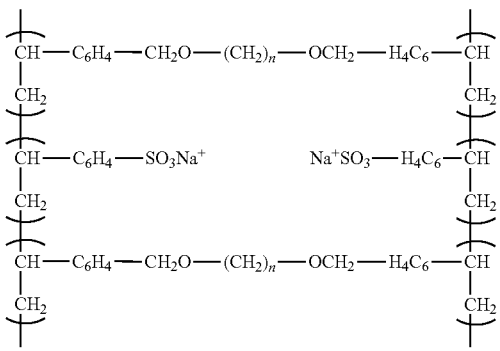

further undergoes ion exchange with an acid solution to produce the crosslinked polymer shown in Structure 10.

Another crosslinked polymer is produced by mixing the desired ratio of SHA with styrene halide comonomer having the formula $CH_2=CH-C_6H_4-SO_2Cl$ or $CH_2=CH-CH_4-SO_2F$, the mixture polymerized under heat or UV light. The intermediate polymer structure shown below

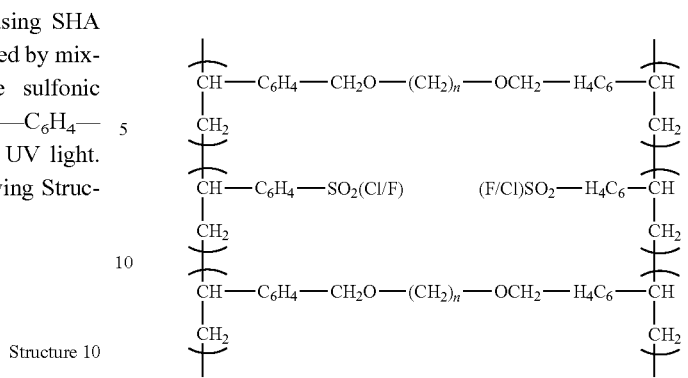

is hydrolyzed with a base/alcohol solution and undergoes ion exchange with an acid solution to produce the crosslinked polymer shown in Structure 10.

To produce the crosslinked polymer shown in Structure 10 with free-radical scavengers, $CH_2=CH-C_6H_4-OH$ or $CH_2=CH-C_6H_4-NH_2$ is added at 1-2 wt % to the mixture during polymerization, resulting in a crosslinked polymer having free-radical scavengers, shown in Structure 11 below:

Structure 11

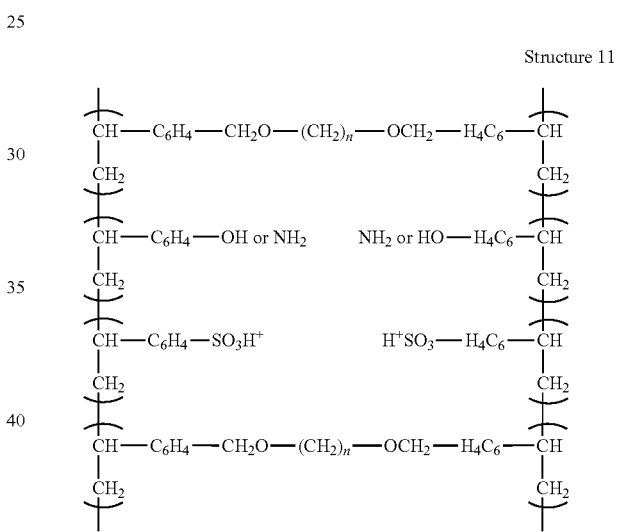

Another crosslinked polymer is produced by mixing the desired ratio of SHA with 4-Bromo benzene comonomer having the formula $CH_2=CH-C_6H_4-Br$, the mixture polymerized under heat or UV light. The intermediate polymer structure shown below

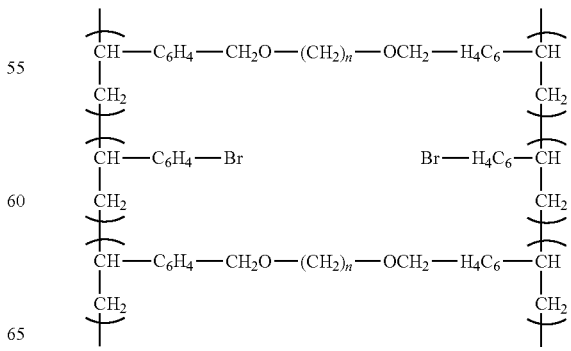

is reacted with I—(CF$_2$)$_m$—O—CF$_2$—CF$_2$—SO$_2$F, where m=2-7, under heat and in the presence of copper or copper oxide catalyst to produce a second intermediate polymer structure shown below in Structure 12:

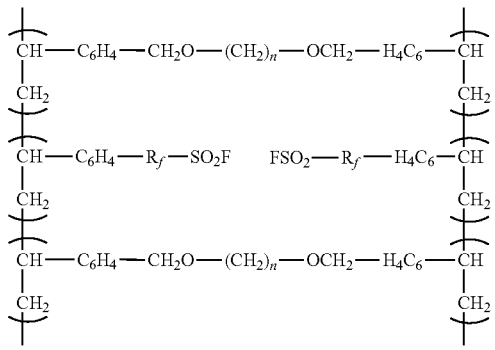

Structure 12

The second intermediate polymer structure is hydrolyzed with a base/alcohol solution and undergoes ion exchange with an acid solution to produce the crosslinked polymer shown in Structure 13 below, where R$_f$=—(CF$_2$)$_m$—O—CF$_2$CF$_2$— and m=2-7.

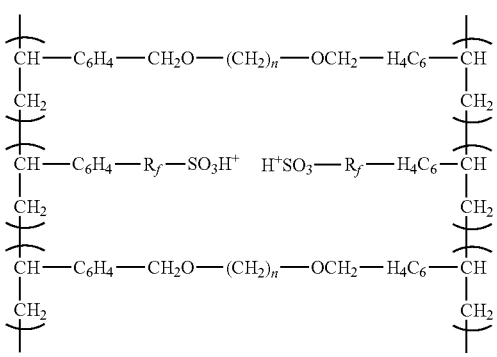

Structure 13

Another crosslinked polymer is produced by mixing the desired ratio of SHA with 4-hydroxy styrene comonomer having the formula CH$_2$=CH—C$_6$H$_4$—OH, the mixture polymerized under heat or UV light. The intermediate polymer structure shown below

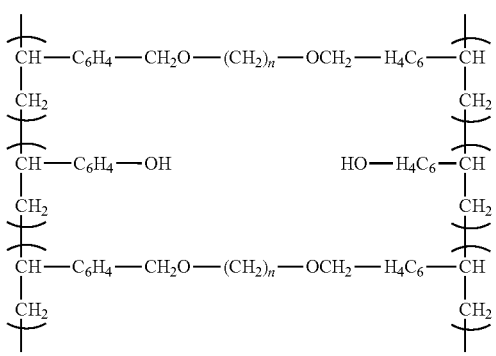

is reacted with I—(CF$_2$)$_m$—O—CF$_2$—CF$_2$—SO$_2$F, where m=2-7, under heat and in the presence of copper or copper oxide catalyst to produce a second intermediate polymer structure shown in Structure 14.

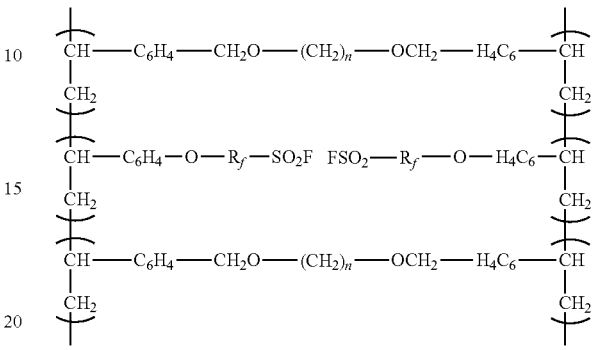

Structure 14

The second intermediate polymer structure is hydrolyzed with a base/alcohol solution and undergoes ion exchange with an acid solution to produce the crosslinked polymer shown in Structure 13, where, again, R$_f$=—(CF$_2$)$_m$—O—CF$_2$CF$_2$— and m=2-7.

To produce the crosslinked polymer shown in Structures 13 or 14 with free-radical scavengers, CH$_2$=CH—C$_6$H$_4$—NH$_2$ is added at 1-2 wt % to the mixture during polymerization, resulting in a crosslinked membrane structure having free-radical scavengers. Structure 15, below, illustrates the crosslinked polymer of Structure 13 with free-radical scavengers:

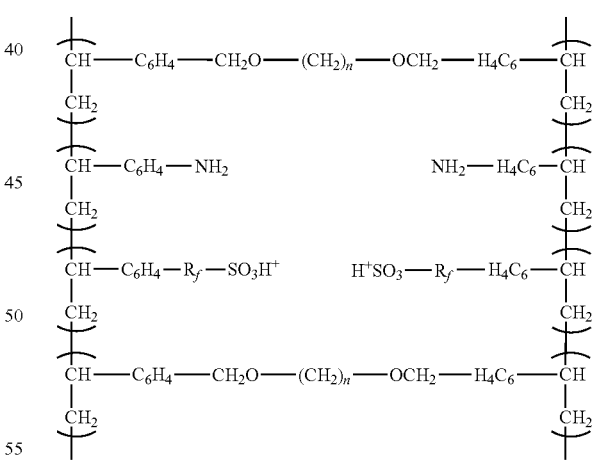

Structure 15

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A polymer electrolyte membrane for a fuel cell comprising a crosslinked polymer produced by polymerizing a styrene-based comonomer with a styrenated crosslinkable monomer comprising the following linear chain formula:

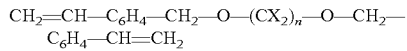

CH$_2$=CH—C$_6$H$_4$—CH$_2$—O—(CX$_2$)$_n$—O—CH$_2$—C$_6$H$_4$—CH=CH$_2$ wherein X is F and n=6-14 or X is H and n=6-18, and the crosslinked polymer has the following Formula A:

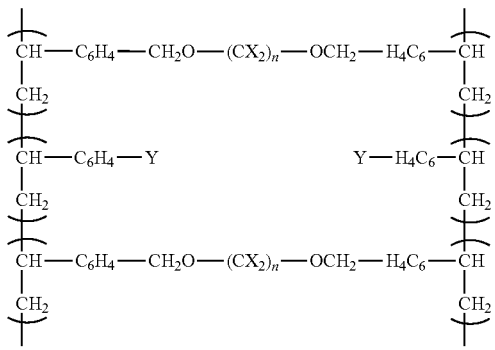

wherein Y is SO$_3$H$^+$ or R$_f$—SO$_3$H$^+$, with R$_f$=—(CF$_2$)$_m$—O—CF$_2$CF$_2$— and m=2-7, wherein R$_f$ is obtained from I—(CF$_2$)$_m$—O—CF$_2$CF$_2$—SO$_2$F, with m=2-7.

2. The polymer electrolyte membrane of claim 1, wherein the crosslinked polymer is a fluorinated crosslinked polymer having the following formula:

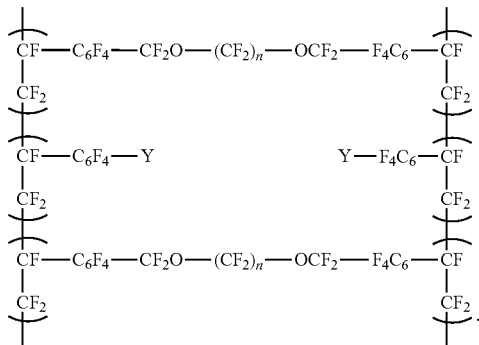

3. The polymer electrolyte membrane of claim 1, wherein the crosslinked polymer is further polymerized with a free radical scavenger.

4. The polymer electrolyte membrane of claim 1, wherein the crosslinked polymer is further polymerized with a free-radical scavenger selected from 4-hydroxy styrene and 4-vinylaniline, the crosslinked polymer having free radical scavengers and shown in the following formula, wherein Z=OH or NH$_2$:

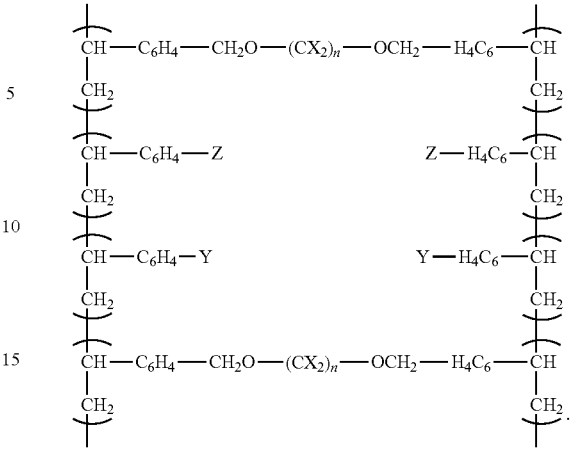

5. The polymer electrolyte membrane of claim 1, wherein the styrenated crosslinkable monomer has X=F, the styrene-based comonomer has the formula CH$_2$=CH—C$_6$H$_4$—SO$_3$H$^+$ and the crosslinked polymer has the Formula A wherein Y=SO$_3$H$^+$.

6. The polymer electrolyte membrane of claim 1, wherein the styrenated crosslinkable monomer has X=F, the styrene-based comonomer has the formula CH$_2$=CH—C$_6$H$_4$—SO$_3$Na$^+$ and the crosslinked polymer has the Formula A wherein Y=SO$_3$H$^+$.

7. The polymer electrolyte membrane of claim 1, wherein the styrenated crosslinkable monomer has X=F, the styrene-based comonomer has the formula CH$_2$=CH—C$_6$H$_4$—SO$_2$Cl or CH$_2$=CH—C$_6$H$_4$—SO$_2$F and the crosslinked polymer has the Formula A wherein Y=SO$_3$H$^+$.

8. The polymer electrolyte membrane of claim 1, wherein the styrenated crosslinkable monomer has X=F, the styrene-based comonomer has the formula CH$_2$=CH—C$_6$H$_4$—Br, and the crosslinked polymer has the Formula A wherein Y=R$_f$—SO$_3$H$^+$, with R$_f$=—(CF$_2$)$_m$—O—CF$_2$CF$_2$— and m=2-7, and wherein R$_f$ is obtained from I—(CF$_2$)$_m$—O—CF$_2$CF$_2$—SO$_2$F, with m=2-7.

9. The polymer electrolyte membrane of claim 1, wherein the styrenated crosslinkable monomer has X=F, the styrene-based comonomer has the formula CH$_2$=CH—C$_6$H$_4$—OH, and the crosslinked polymer has the Formula A wherein Y=—O—R$_f$—SO$_3$H$^+$ with R$_f$=—(CF$_2$)$_m$—O—CF$_2$CF$_2$— and m=2-7, and wherein R$_f$ is obtained from I—(CF$_2$)$_m$—O—CF$_2$CF$_2$—SO$_2$F, with m=2-7.

10. The polymer electrolyte membrane of claim 1, wherein the styrenated crosslinkable monomer has X=H, the styrene-based comonomer has the formula CH$_2$=CH—C$_6$H$_4$—SO$_3$H$^+$ and the crosslinked polymer has the Formula A wherein Y=SO$_3$H$^+$.

11. The polymer electrolyte membrane of claim 1, wherein the styrenated crosslinkable monomer has X=H, the styrene-based comonomer has the formula CH$_2$=CH—C$_6$H$_4$—SO$_3$Na$^+$ and the crosslinked polymer has the Formula A wherein Y=SO$_3$H$^+$.

12. The polymer electrolyte membrane of claim 1, wherein the styrenated crosslinkable monomer has X=H, the styrene-based comonomer has the formula CH$_2$=CH—C$_6$H$_4$—SO$_2$Cl or CH$_2$=CH—C$_6$H$_4$—SO$_2$F and the crosslinked polymer has the Formula A wherein Y=SO$_3$H$^+$.

13. The polymer electrolyte membrane of claim 1, wherein the styrenated crosslinkable monomer has X=H, the styrene-based comonomer has the formula CH$_2$=CH—C$_6$H$_4$—Br, and the crosslinked polymer has the Formula A wherein $Y=R_f-SO_3H^+$, with $R_f=(CF_2)_m-O-CF_2CF_2-$ and m=2-7, and wherein $R_f$ is obtained from $I-(CF_2)_m-O-CF_2CF_2-SO_2F$, with m=2-7.

14. The polymer electrolyte membrane of claim 1, wherein the styrenated crosslinkable monomer has X=H, the styrene-based comonomer has the formula $CH_2=CH-C_6H_4-OH$, and the crosslinked polymer has the Formula A wherein $Y=-O-R_f-SO_3H^+$ with $R_f=(CF_2)_m-O-CF_2CF_2-$ and m=2-7, and wherein $R_f$ is obtained from $I-(CF_2)_m-O-CF_2CF_2-SO_2F$, with m=2-7.

15. The polymer electrolyte membrane of claim 1 further comprising a porous support on which the crosslinked polymer is supported.

16. A styrenated crosslinkable monomer comprising the following formula:

$$CH_2=CH-C_6H_4-CH_2-O-(CX_2)_n-O-CH_2-C_6H_4-CH=CH_2$$

wherein X is H, produced by functionalizing a linear chain diol with styrene, the linear chain diol having the following formula:

$$OH-CH_2-(CF_2)_n-CH_2-OH$$

wherein n=7-18.

17. A styrenated crosslinkable monomer comprising the following formula:

$$CH_2=CH-C_6H_4-CH_2-O-(CX_2)_n-O-CH_2-C_6H_4-CH=CH_2$$

wherein X=F, produced by functionalizing a linear chain diol with styrene, the linear chain diol having the following formula:

$$OH-CH_2-(CF_2)_n-CH_2-OH$$

wherein n=6-14.

18. The styrenated crosslinkable monomer of claim 17, wherein the linear chain diol is mixed with vinyl benzyl chloride to functionalize the linear chain diol.

* * * * *